(12) United States Patent
Schulman et al.

(10) Patent No.: US 7,107,103 B2
(45) Date of Patent: Sep. 12, 2006

(54) FULL-BODY CHARGER FOR BATTERY-POWERED PATIENT IMPLANTABLE DEVICE

(75) Inventors: Joseph H. Schulman, Santa Clarita, CA (US); Carla Mann, Los Angeles, CA (US); Lee J. Mandell, West Hills, CA (US)

(73) Assignee: Alfred E. Mann Foundation for Scientific Research, Santa Clara, CA (US)

( * ) Notice: Subject to any disclaimer, the term of this patent is extended or adjusted under 35 U.S.C. 154(b) by 554 days.

(21) Appl. No.: 10/272,229

(22) Filed: Oct. 16, 2002

(65) Prior Publication Data

US 2003/0078634 A1   Apr. 24, 2003

Related U.S. Application Data

(60) Continuation-in-part of application No. 09/677,384, filed on Sep. 30, 2000, now Pat. No. 6,564,807, which is a division of application No. 09/048,827, filed on Mar. 25, 1998, now Pat. No. 6,164,284, which is a continuation-in-part of application No. 09/030,106, filed on Feb. 25, 1998, now Pat. No. 6,185,452.

(60) Provisional application No. 60/347,902, filed on Oct. 18, 2001, provisional application No. 60/042,447, filed on Mar. 27, 1997, provisional application No. 60/039,164, filed on Feb. 26, 1997.

(51) Int. Cl.
*A61N 1/30* (2006.01)
*A61N 1/378* (2006.01)

(52) U.S. Cl. ............... 607/61; 607/33; 604/20
(58) Field of Classification Search .......... 607/27, 607/29–33, 60–62
See application file for complete search history.

(56) References Cited

U.S. PATENT DOCUMENTS

| 5,193,539 | A | | 3/1993 | Schulman et al. |
|---|---|---|---|---|
| 5,193,540 | A | | 3/1993 | Schulman et al. |
| 5,312,439 | A | | 5/1994 | Loeb |
| 5,324,316 | A | | 6/1994 | Schulman et al. |
| 5,358,514 | A | | 10/1994 | Schulman et al. |
| 5,405,367 | A | | 4/1995 | Schulman et al. |
| 5,729,129 | A | | 3/1998 | Acker |
| 6,051,017 | A | | 4/2000 | Loeb et al. |
| 6,148,235 | A | * | 11/2000 | Kuiper ................ 607/29 |
| 6,164,284 | A | * | 12/2000 | Schulman et al. .......... 128/899 |
| 6,175,764 | B1 | | 1/2001 | Loeb et al. |

(Continued)

OTHER PUBLICATIONS

Loeb, et al, Bion System for Distributed Neural Prosthetic Interfaces, 2001, pp. 1-23, Publisher: Journal of Medical Engineering and Physics, Published in: Los Angeles, CA.

*Primary Examiner*—Robert E Pezzuto
*Assistant Examiner*—Frances P. Oropeza
(74) *Attorney, Agent, or Firm*—Malcolm J. Romano (57) ABSTRACT

A full-body charger for charging one or more battery-powered devices wherein such devices are configured for implanting beneath a patient's skin for the purpose of tissue, e.g., nerve or muscle, stimulation and/or parameter monitoring and/or data communication. Devices in accordance with the invention include a support structure, typically chair-shaped or bed-shaped, capable of supporting a patient's body while providing a magnetic field to one or more of the implanted devices using one or more coils mounted within for providing power to the implanted devices. Consequently, in a preferred embodiment, a single, generally sequential, charging cycle can charge all of the implanted devices and thus minimize the charge time requirements for a patient and accordingly improve the patient's life style.

20 Claims, 10 Drawing Sheets

U.S. PATENT DOCUMENTS

| | | | |
|---|---|---|---|
| 6,181,965 B1 | 1/2001 | Loeb et al. | |
| 6,185,452 B1 * | 2/2001 | Schulman et al. | 604/20 |
| 6,185,455 B1 | 2/2001 | Loeb et al. | |
| 6,208,894 B1 | 3/2001 | Schulman et al. | |
| 6,212,430 B1 | 4/2001 | Kung | |
| 6,240,316 B1 | 5/2001 | Richmond et al. | |
| 6,281,661 B1 * | 8/2001 | Kaite et al. | 320/116 |
| 6,315,721 B1 | 11/2001 | Schulman et al. | |
| 6,345,202 B1 | 2/2002 | Richmond et al. | |
| 6,369,577 B1 * | 4/2002 | Cho | 324/426 |
| 6,400,991 B1 * | 6/2002 | Kung | 607/61 |
| 6,443,891 B1 * | 9/2002 | Grevious | 600/302 |
| 6,650,943 B1 | 11/2003 | Whitehurst et al. | |
| 6,658,301 B1 | 12/2003 | Loeb et al. | |
| 6,845,267 B1 | 1/2005 | Harrison et al. | |
| 2003/0093131 A1 | 5/2003 | Loeb et al. | |
| 2003/0236557 A1 | 12/2003 | Whitehurst et al. | |
| 2003/0236558 A1 | 12/2003 | Whitehurst et al. | |
| 2004/0015204 A1 | 1/2004 | Whitehurst et al. | |
| 2004/0015205 A1 | 1/2004 | Whitehurst et al. | |
| 2004/0082978 A1 | 4/2004 | Harrison et al. | |
| 2005/0021108 A1 | 1/2005 | Klostorman et al. | |
| 2005/0033375 A1 | 2/2005 | Marchad et al. | |

* cited by examiner

FIG. 1

PRIOR ART

FIG. 2

PRIOR ART

PRIOR ART

FULL-BODY CHARGER FOR BATTERY-POWERED PATIENT IMPLANTABLE DEVICE

This application is a continuation-in-part of U.S. patent application Ser. No. 09/677,384, filed Sep. 30, 2000, now U.S. Pat. No. 6,564,807. U.S. Pat. No. 6,564,807 is a divisional of U.S. patent application Ser. No. 09/048,827, filed Mar. 25, 1998, now U.S. Pat. No. 6,164,284. U.S. Pat. No. 6,164,284 is a continuation-in-part of U.S. patent application Ser. No. 09/030,106, filed Feb. 25, 1998, now U.S. Pat. No. 6,185,452, and claims the benefit of U.S. Provisional Application No. 60/042,447, filed Mar. 27, 1997. U.S. Pat. No. 6,185,452 claims the benefit of U.S. Provisional Application No. 60/039,164, filed Feb. 26, 1997. Furthermore, the present application claims the benefit of U.S. Provisional Application No. 60/347,902, filed Oct. 18, 2001.

FIELD OF THE INVENTION

The present invention is generally directed to chargers for charging implantable battery-powered medical devices and more particularly to chargers which can charge a plurality of such devices.

BACKGROUND OF THE INVENTION

The present invention relates to implantable medical devices for stimulating body tissue and sensing body parameters (i.e., microstimulators and microsensors) as are known in the art. See, e.g., U.S. Pat. Nos. 5,193,539; 5,193,540; 5,312,439; 5,324,316; 5,358,514; and 5,405,367; each of which is incorporated herein by reference in its entirety. Generally, such implantable devices are referred to herein as microdevices.

Such implantable microdevices are characterized by a sealed housing which contains electronic circuitry for producing small electric currents between spaced electrodes (or sensing body parameters via the spaced electrodes). By precisely implanting the microdevices proximate to targeted tissue, the currents will stimulate the tissue or sense a physiological parameter and thus such devices produce medically beneficial results.

Typically, such microdevices derive operating power from an internal coil that is inductively coupled to an external AC magnetic field produced, for example, by a drive coil placed proximate to the microdevice(s). An AC voltage induced in the internal coil of the microdevice is rectified and filtered to produce a DC operating voltage which is used to power the electronic circuitry or power a battery contained within which in turn powers the electronic circuitry. Such an arrangement requires that the user remain in close proximity to the drive coil to maintain sufficient power transfer to operate the microdevice, e.g., to maintain tissue stimulation.

Alternatively, such microdevices can operate from power received from an internal rechargeable battery. See, e.g., U.S. Pat. Nos. 6,164,284; 6,185,452; 6,208,894; and 6,315,721; each of which is incorporated herein by reference in its entirety. Such battery-powered devices can, dependent upon the treatment regimen, be distributed throughout a patient's body. While such battery-powered devices free the user from always remaining in close proximity to the drive coil (to maintain operation of the device), each such rechargeable device still requires periodic charging.

SUMMARY OF THE INVENTION

The present invention is directed to a full-body charger for charging one or more battery-powered devices which are configured for implanting beneath a patient's skin for the purpose of tissue, e.g., nerve or muscle, stimulation and/or parameter monitoring and/or data communication. Devices in accordance with the invention include a support structure, typically chair-shaped or bed-shaped, e.g., mattress-shaped, capable of supporting a patient's body while providing a magnetic field to one or more of the implanted devices using one or more coils mounted within or on the support structure. Consequently, in a preferred embodiment, all of the implanted devices can be charged during a single charging cycle and thus, the present invention minimizes the effort and charge time requirements for a patient and accordingly improves the patient's life style.

In accordance with a preferred embodiment of the present invention, a full-body charger for providing an alternating magnetic field to one or more electrically-powered devices implanted beneath the skin of a patient's body (wherein each of the electrically-powered devices is powered by a rechargeable battery mounted within each device) comprises: (1) a support structure configured to support a patient's body, (2) at least one coil configured for mounting within the support structure, proximate to one or more of the electrically-powered devices, for emitting a magnetic field substantially encompassing one or more of the electrically-powered devices implanted within the patient's body, and (4) a controller for periodically providing an AC signal to energize at least one of the coils, and wherein the controller additionally includes communication circuitry for periodically providing a control signal to the electrically-powered devices to selectively interrogate the status of the rechargeable battery mounted within and for receiving a status signal in response thereto.

In accordance with a significant aspect of the invention, the full-body charger communicates with each of the implanted devices, preferably by modulating the AC signal used to power the coil or otherwise emitting a modulated output signal from a transducer, to determine the status of the rechargeable battery mounted within each implanted device.

In a further aspect of the present invention, a plurality of coils may be located within (or proximate to) the support structure and the coils may be periodically, sequentially energized to charge implanted devices proximate to each coil. Accordingly, the fields emitted from any one coil will not interfere with the charging fields or communication signals of any other coil.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The present invention is directed to a charging system for devices that are configured for implanting beneath a patient's skin for the purpose of tissue, e.g., nerve or muscle, stimulation and/or parameter monitoring and/or data communication. Devices for use with the present invention are comprised of a sealed housing, preferably having an axial dimension of less than 60 mm and a lateral dimension of less than 6 mm, containing a power source and power consuming circuitry including a controller, an address storage means, a data signal receiver and an input/output transducer. When used as a stimulator, such a device is useful in a wide variety of applications to stimulate nerves, muscles, and/or associated neural pathways, e.g., to decrease or relieve pain, stimulate specific muscles or organs to better carry out a body function (e.g., to exercise weak or unconditioned muscles or to control urinary incontinence), and the like. Preferably such implantable microdevices are individually addressable for control purposes via a magnetic, propagated RF wave, or ultrasonic signal.

Figure 1:
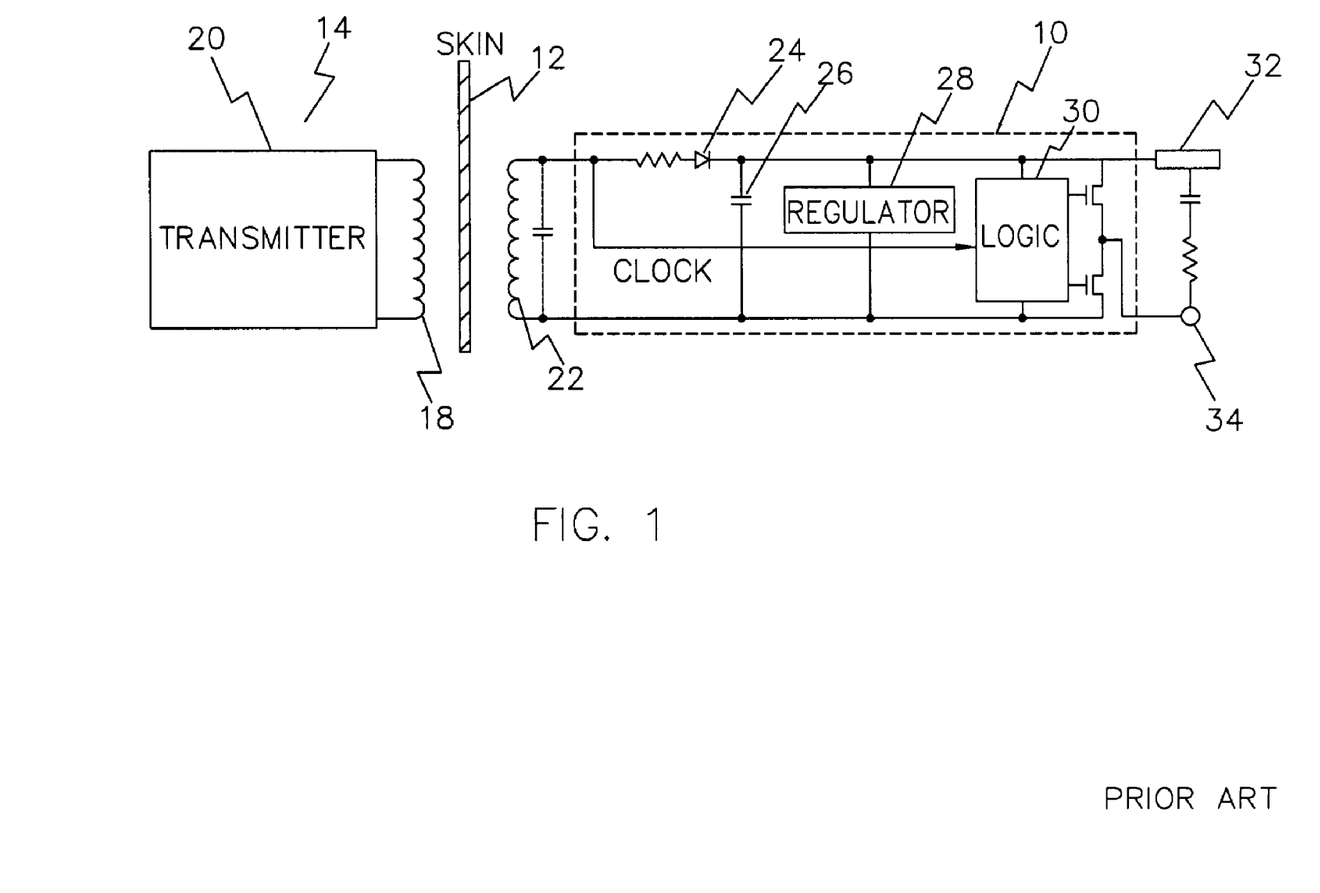
FIG. 1 illustrates a block diagram of an RF-powered microstimulator as known in the prior art.

FIG. 1 shows an exemplary prior art implantable stimulator 10 (as shown in FIG. 1 of the aforementioned U.S. Pat. No. 6,185,452) implanted beneath a patient's skin 12 that receives power from an externally located power supply 14 via an alternating magnetic field generated by an externally mounted coil 18 that is energized by a transmitter 20. Within the stimulator 10, the magnetic field generates an AC current in a coil 22 that is rectified by rectifier 24 and stored in a capacitor 26 in conjunction with a regulator 28 to generate a voltage that powers its logic 30. The logic 30 is then used to generate a stimulation current between electrodes 32 and 34. A capacitor (not shown) is preferably used in series with electrode 32 or 34 to isolate the body tissue from any DC current. Since the control logic 30 relies upon power stored in the capacitor 26 to supply its operating power, it typically stops functioning in a short period of time after the external power supply 14 is removed as the charge stored in capacitor 26 is depleted. Consequently, when such a stimulator 10 is used in an application which requires continuous stimulation, e.g., for blocking pain in a neural pathway, the continuous presence and activation of the external power supply 14 is required. While such a continuous presence can be achieved by use of a portable power supply, its physical presence can be considered as a life style limitation.

Figure 2:
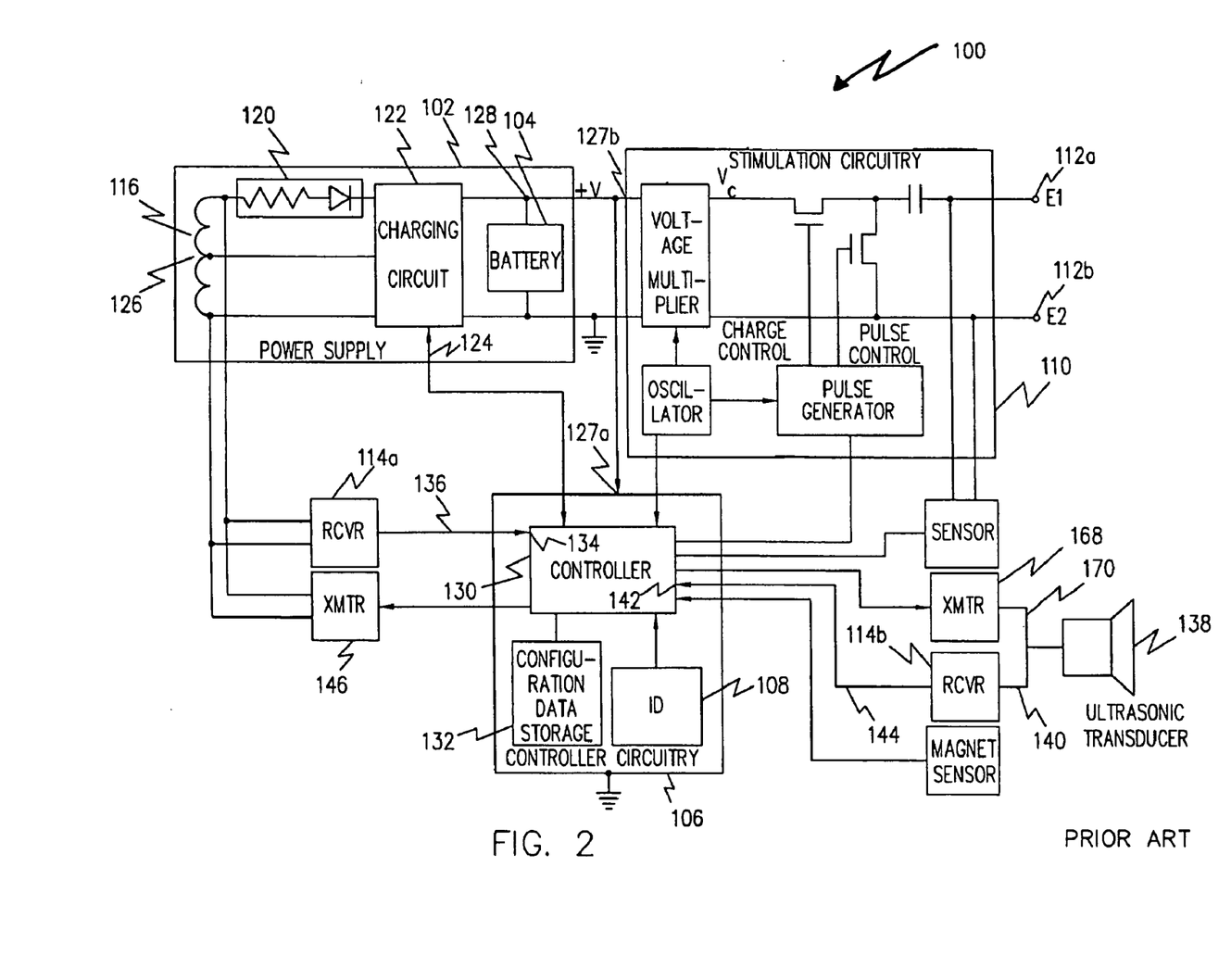
FIG. 2 comprises a block diagram of an exemplary device as known in the prior art, for use with the present invention, that includes a battery for powering the device for a period of time in excess of one hour in response to a charging from an external controller.

In contrast, FIG. 2 (FIG. 3A of the aforementioned U.S. Pat. No. 6,164,284) shows a block diagram of an electrically-powered implantable device 100 for use with the present invention (configured as a microstimulator) that can stimulate tissue (e.g., a neural pathway, nerve or muscle) for a prolonged period of time, i.e., in excess of one hour, without requiring the continuous use of an external power source. Consequently, in an exemplary application, a preferred microstimulator 100 can be used to block pain in a selected nerve for a prolonged period of time, long after the external power source has been removed. The exemplary microstimulator is comprised of a sealed housing for enclosing a power supply 102, e.g., a rechargeable battery 104, and power consuming electronic circuitry including (1) controller circuitry 106 powered by the power supply 102 and having address storage circuitry 108 with an identification address (ID) stored within, (2) stimulation circuitry 110 powered by the power supply 102 and operating under control of the controller circuitry 106 for providing drive pulses to electrodes 112a and 112b, and (3) receiver means 114a and/or 114b for providing command and address identification information to the controller circuitry 106.

In a preferred implementation, the power supply 102 comprises a rechargeable battery 104 used in conjunction with a charging circuit 122 to provide sufficient power for prolonged activation of the controller circuitry 106 and the stimulation circuitry 110. See, e.g., U.S. Pat. Nos. 6,164,284; 6,185,452; 6,208,894; and 6,315,721; which are incorporated herein by reference in their entirety.

Figure 3A:
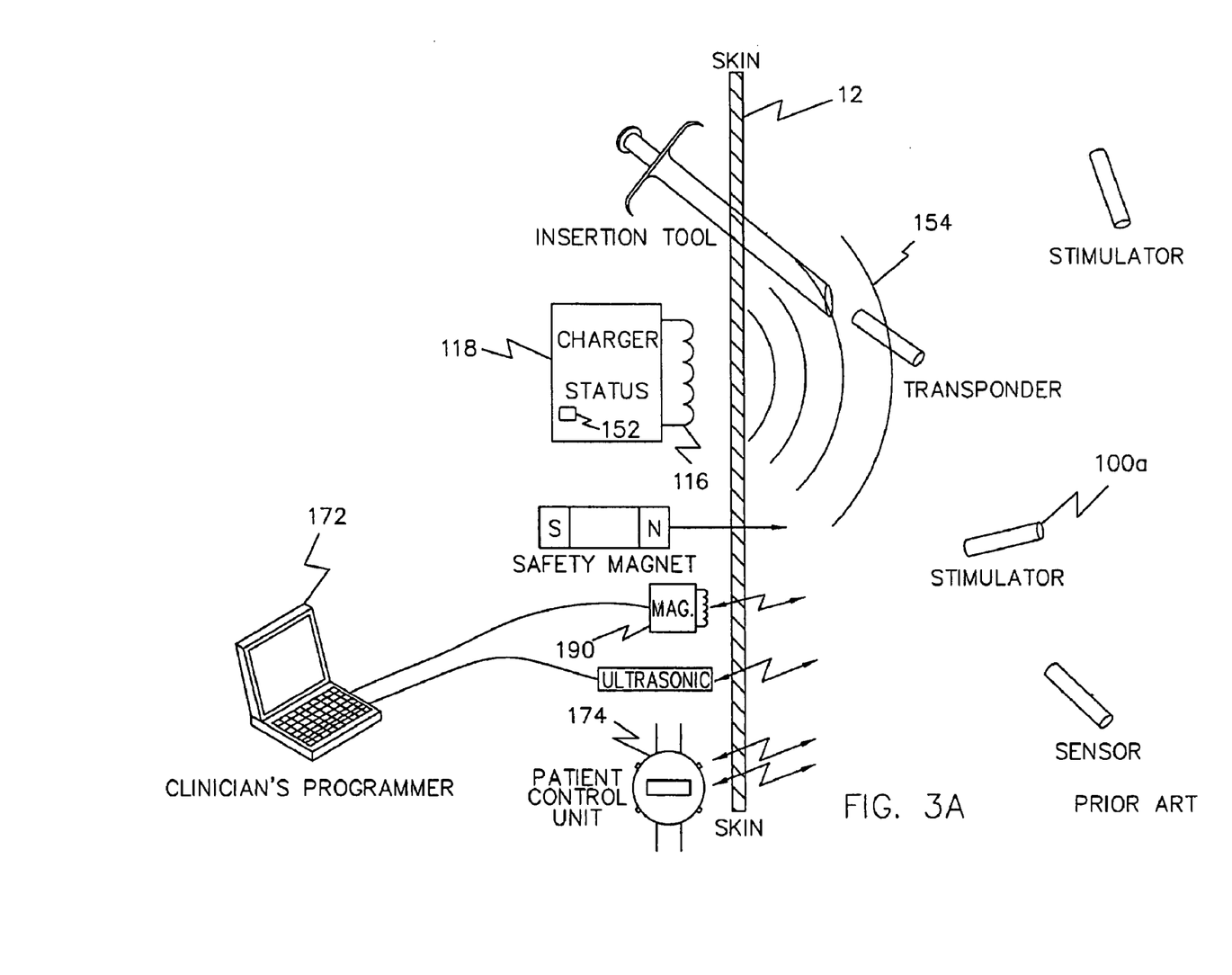
FIG. 3A is a simplified functional block diagram of the use of the exemplary implanted devices (microstimulators, microsensors and microtransponders) as known in the prior art in an environment where they are recharged and controlled from devices external to a patient's body.

In operation, a coil 116 receives power in the form of an alternating magnetic field generated from an external power source 118 (see FIG. 3A which essentially corresponds to FIG. 3A of the aforementioned U.S. Pat. No. 6,184,284) and responsively supplies an AC current to a rectifier 120 which is passed as a rectified DC current to a charging circuit 122. The charging circuit 122 then monitors the voltage +V on battery 104 and charges it according to its preferred charging characteristics (current and voltage). As discussed further below, the charging circuit 122 preferably communicates via path 124 with the controller circuitry 106 which in turn periodically communicates with the external power source 118 via a magnetic, ultrasonic, or propagated RF signal.

In a typical application (see FIG. 3A), a plurality of such devices 100, e.g., microstimulators, are implanted under the skin 12 of a patient's body and simultaneously subjected to an alternating magnetic field 154 from the external power source 118. Accordingly, once the charging circuit 122 determines that battery 104 has been sufficiently charged, the charging circuit 122 preferably detunes coil 116, e.g., by shunting out center tap 126 (or adding a capacitor across the coil), and thus minimizes any heat generation in the charging circuit 122 or any detrimental effects to the battery 104 from overcharging (including heat generation). Thus, the external power source 118 can continue to provide charging power via an alternating magnetic field indefinitely. However in one preferred embodiment, the external power source periodically polls the implanted devices for status information and continues to provide charging power until it has received status information from each of the implanted devices 100 that its battery 104 is charged (or at least those devices within its operational, i.e., communication/charging, range).

Both the controller circuitry 106 (via power input terminal 127a) and stimulation circuitry 110 (via power input terminal 127b) receive power from the battery 104 power output terminal 128. The power dissipation of circuitry within the implanted device 100 is minimized by the use of CMOS and other low power logic. Accordingly, the required capacity of the battery 104 is minimized.

The controller circuitry 106 controls the operation of the stimulation circuitry 110 using a controller 130 (preferably a state machine or microprocessor) according to configuration data within a configuration data storage 132 coupled to controller 130. The configuration data specifies various programmable parameters that effect the characteristics of the drive pulses generated by stimulation circuitry 110 as controlled by the controller 130. Preferably, each implanted device 100, e.g., microstimulator, can be actuated (enabled/disabled) or have its characteristics altered via communications with one or more devices external to itself. Accordingly, each implanted device 100 uses its address storage circuitry 108, e.g., an EEPROM, PROM, or other nonvolatile storage device programmed during manufacture, to identify itself (e.g., using an ID code comprised of 8 or more bits stored within). Alternatively, the address storage circuitry 108 can be comprised of a portion of an integrated circuit that is mask programmed to form all or a portion of the ID and/or the use of a laser trimming process to designate all or the remaining portion of the ID. In a further alternative implementation, the ID can be designated by a selection of jumpers, e.g., wire bonds, used individually or in combination with the use of a laser trimming process. In operation, an external device (e.g., charger 118) transmits a modulated magnetic, ultrasonic, or propagated RF command signal containing command information that includes an address field. When the implanted device 100 receives and demodulates this command signal to receive the command information within, it first determines whether there is a match to its address within its address storage circuitry 108 before processing the rest of its data. Otherwise, the command information is ignored.

In one configuration, alternating magnetic field 154 is amplitude modulated with this command signal. Receiver circuitry 114a detects and demodulates this command signal by monitoring the signal generated across coil 116 (preferably the same coil used for charging the rechargeable battery 104). The demodulated data is provided to a controller data input 134 via path 136 where its applicability to a particular implanted device 100 is determined. Alternatively, the command signal can modulate a propagated RF signal which can be detected in a similar manner by receiver 114a (configured to demodulate an RF signal) using coil 116 as an antenna or using a separate antenna, e.g., via electrodes 112a, 112b. Various modulation techniques may be used including, but not limited to, amplitude modulation, frequency modulation, quadrature amplitude modulation (QAM), frequency shift keying (FSK), quad phase, etc.

In a next configuration, an ultrasonic signal can be used to deliver this command signal to each implanted device 100. In this configuration, an ultrasonic transducer 138 located within the device 100 generates a signal 140 which is demodulated by ultrasonic demodulator 114b. This demodulated signal is then provided to an ultrasonic data input 142 via path 144 and processed in a manner similar to that described in reference to a magnetic signal. The ultrasonic implementation provides significant advantages in that a patient's body is primarily comprised of fluid and tissue that is conducive to passing an ultrasonic signal. Consequently, a control device located anywhere inside (or external but in contact with) the patient's body can communicate with each device 100 implanted within.

Figure 3B:
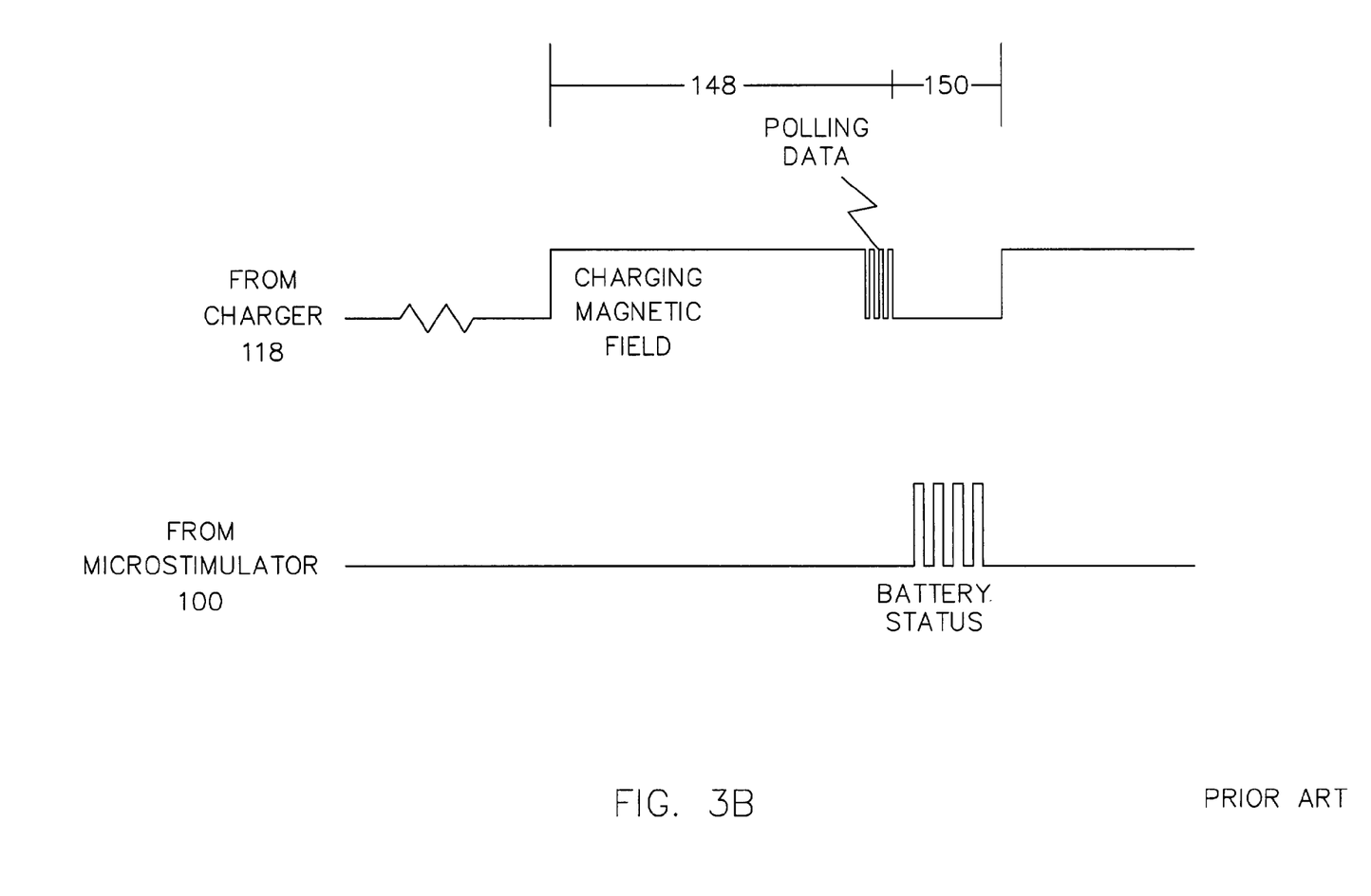
FIG. 3B shows a simplified timing diagram as known in the prior art showing periodic breaks in the generation of the charging magnetic field to selectively interrogate the battery status of the exemplary implanted devices.

In a preferred embodiment, the implanted device 100 includes means for transmitting status and data to external devices. In an exemplary charging mode, it is preferable that each device 100 can individually communicate with charger 118 so that charger 118 can determine when all of the implanted devices 100 (or at least those within its operational, i.e., charging/communication, range) have been fully charged. Preferably, device 100 includes transmitter means to emit a magnetic signal modulated with this data. This transmitter means comprises modulator circuitry 146 which modulates, e.g., amplitude modulates, an AC voltage and delivers this modulated signal to coil 116 which emits a modulated magnetic signal. While this modulated signal can use a different carrier frequency from that of the AC signal used by the charger 118, it is preferable that the communication channel, e.g., the magnetic field 154 between the devices, be time-shared. In FIG. 3B, the charger 118 emits an alternating magnetic field for a first time period 148. At the end of the first time period 148, this alternating magnetic field is modulated (e.g., amplitude modulated) with a series of bits corresponding to polling data corresponding to a selected implanted device 100 (i.e., including an address for one implanted device 100). The charger 118 then goes into a receive mode for a second time period 150 during which time the selected device 100 emits a magnetic signal modulated with a series of bits corresponding to its battery status. This charging/polling cycle preferably repeats for all of the implanted devices within the operational range of the charger 118. Once the charger 118 determines that all of the devices 100 have been charged, the cycle is terminated and the patient or clinician is preferably notified, e.g., using a visual or audio annunciator 152 (see FIG. 3A).

Figure 4:
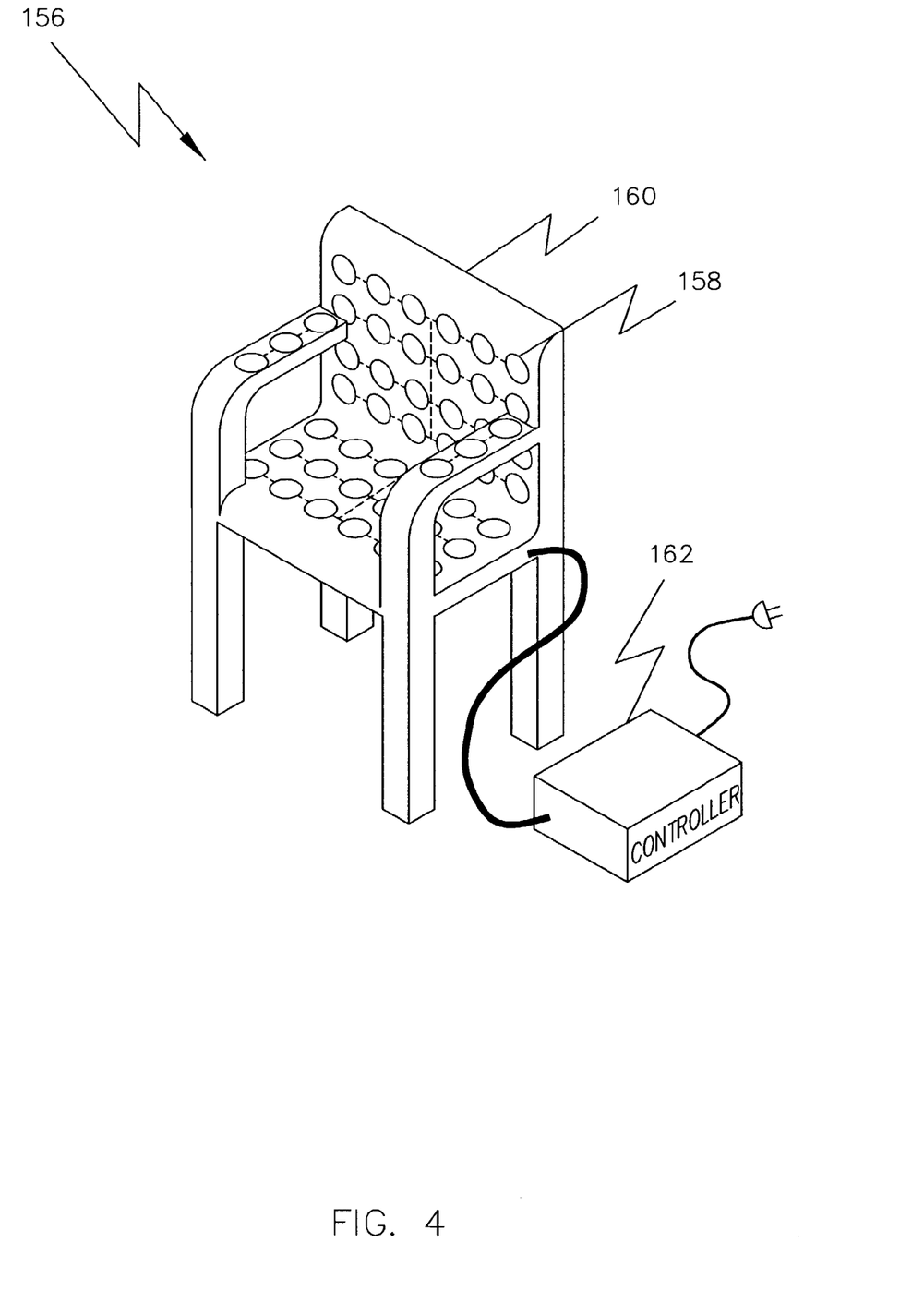
FIGS. 4 and 5 comprise diagrams of a support structure charging apparatus of the present invention configured as either a chair-shaped or bed-shaped, e.g., mattress-shaped, structure having at least one coil implanted within or on its surface such that the support structure can support a patient's body for a prolonged period of time while generating alternating magnetic fields of sufficient distribution and magnitude to encompass all of the implanted devices in the patient's body.
Figure 5:
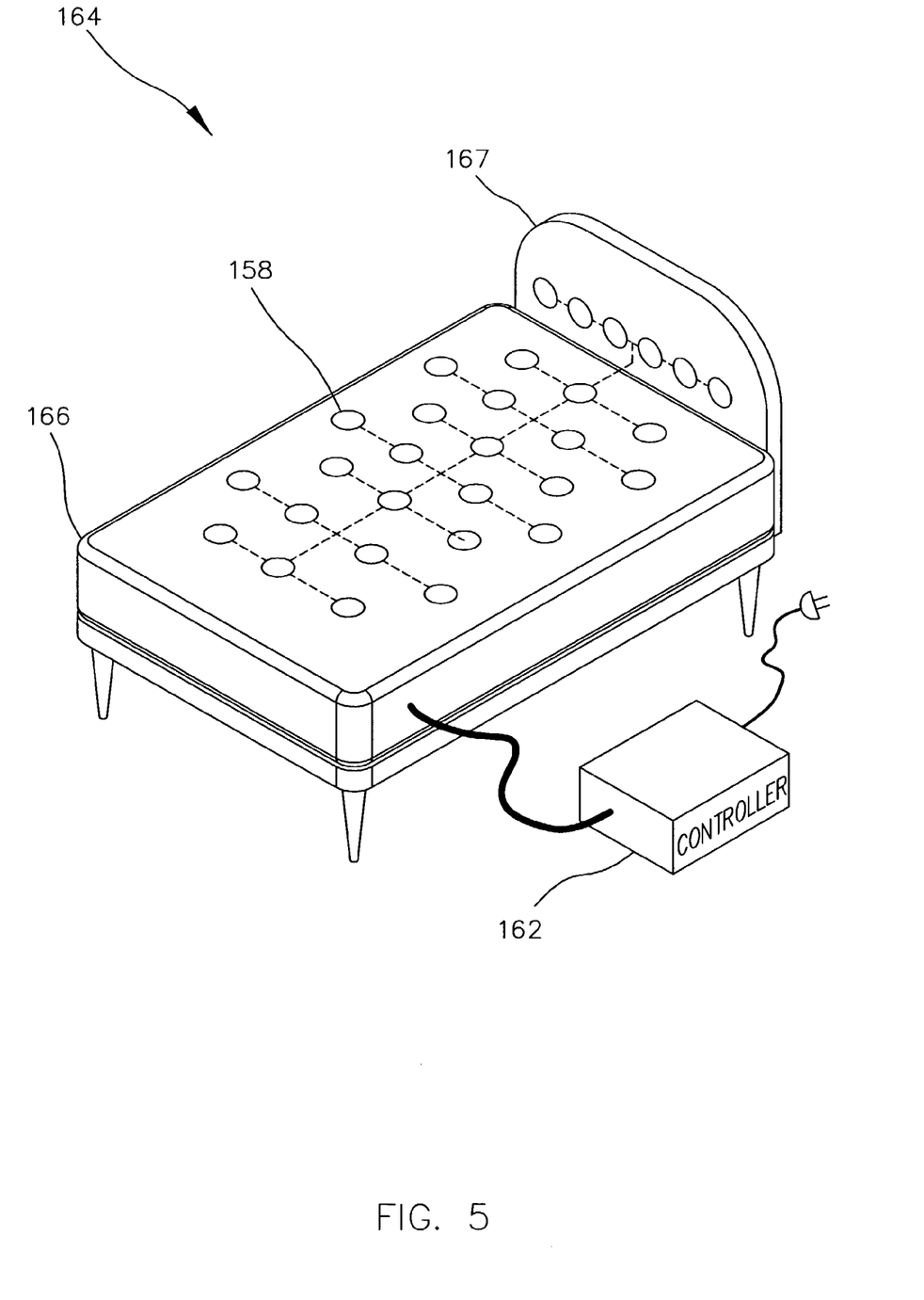
Figure 6:
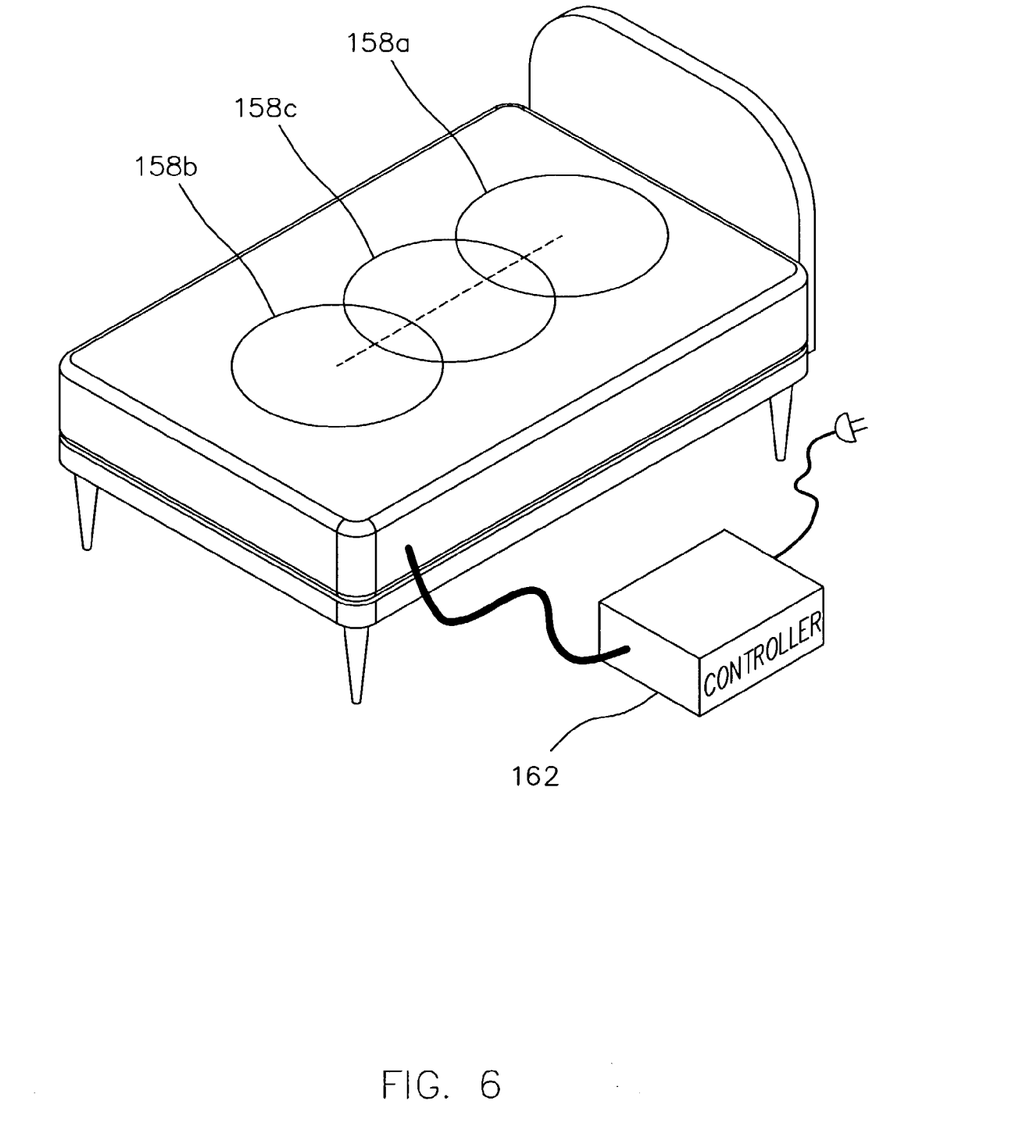
FIG. 6 shows an alternative distribution of the coils of FIGS. 4 and 5 that uses larger and potentially overlapping coils to cover the required area. The larger coils typically require larger drive currents but fewer switches between the coils will be needed.

Depending upon the number of implanted devices 100, their distribution within the patient's body and the magnitude of the magnetic field 154 emitted from the charger 118, the charger 118 may need to be relocated and additional charge cycles instituted to charge all of the devices 100. To simplify this procedure, the present invention is directed to a "full-body" charger that can charge all of the implanted devices 100 within a patient within a single charging cycle. (For the purpose of this application, a charging cycle corresponds to a single use of a charger 118 which may and generally does comprise a plurality of multiple on, off, and inquiry sequences of the charge coil 116 and communication channel.) Generally, the charging fields presented between two nearby coils will interfere with each other (dependent upon their separation). Accordingly, embodiments of the present invention, generally sequentially energize coils to avoid such interference. Advantageously, a single controller 162 with control switches (not shown) can power multiple coils (one at a time). Two exemplary "full-body" embodiments of chargers are shown in FIGS. 4 and 5. In a first full-body embodiment 156 shown in FIG. 4, one or more charging coils 158 are located on or embedded within a chair-shaped structure 160 which supports a patient's body. The controller 162, preferably AC powered, is coupled (preferably bidirectionally) to the charging coils 158 and controls the charging cycle of FIG. 3B, preferably individually controlling coils 158 in response to status signals received from the implanted devices 100. The charging cycle can now encompass all implanted devices 100 with a magnetic field that is essentially evenly-distributed throughout the patient's body (or at least distributed over the portions of the patient's body having the implantable devices 100 that periodically require rechargings). Preferably, the controller 162 receives battery status signals via the coils 158 and uses these status signals to control/terminate the charging cycle as needed. In a second full-body embodiment 164 of FIG. 5, a bed-shaped structure 166 with one or more charging coils 158 located on or embedded within can similarly support a patient's body for the duration of the charging cycle. Additionally, coils 158 may be distributed on or within a headboard 167 of the bed-shaped structure 166. FIG. 6 shows an alternative coil arrangement suitable for any support structure embodiment, e.g., 156 or 164, in which the coils are larger. Typically larger coils or combinations of smaller coils will require more drive power but cover the required area in less iterations. Accordingly, use of this variation is a design choice. In this variation, coil 158*c* physically overlaps portions of coils 158*b* and 158*a*. Accordingly, power to these coils must be sequentially powered, (e.g., 158*a* then 158*b* then 158*c*, or 158*a* then 158*c* then 158*b*, etc.) to avoid interactions of their magnetic fields.

Alternatively, ultrasonic means can be used to communicate status or other data from the implanted device 100 to an external device. In such an embodiment, an ultrasonic transmitter 168 under control of the controller 130 generates a modulated signal on line 170 that is emitted by ultrasonic transducer 138. As previously discussed, an ultrasonic signal efficiently passes through the body fluids and tissues and as such is a preferred communication means for communication between devices implanted within the patient's body, e.g., other microstimulators 100, and suitable for communication with external devices in contact with the patient's skin 12.

The use of magnetic or ultrasonic communication, i.e., transmitter and receiver, means are not mutually exclusive and in fact implanted devices 100 may include both. For example as shown in FIG. 3A, a clinician's programmer 172 (a device for primarily programming the operation of the implanted devices 100), can communicate with a microstimulator 100*a* using a modulated magnetic signal from magnetic emitter 190 and periodically receive a modulated magnetic signal from microstimulator 100*a* reflecting its battery status. When a magnetic means of communication is used during a charging mode, a patient control unit 174 (e.g., a device in direct contact with the skin, typically in the form of a "wrist watch", primarily used for monitoring the status of the implanted devices 100) will preferably communicate using ultrasonic means. Additionally, communication between implanted microstimulators 100 is also desirable, e.g., in a master-slave or transponder-slave configuration. For these modes, ultrasonic means are preferable since ultrasonic signals efficiently pass through the body fluids.

Figure 7:
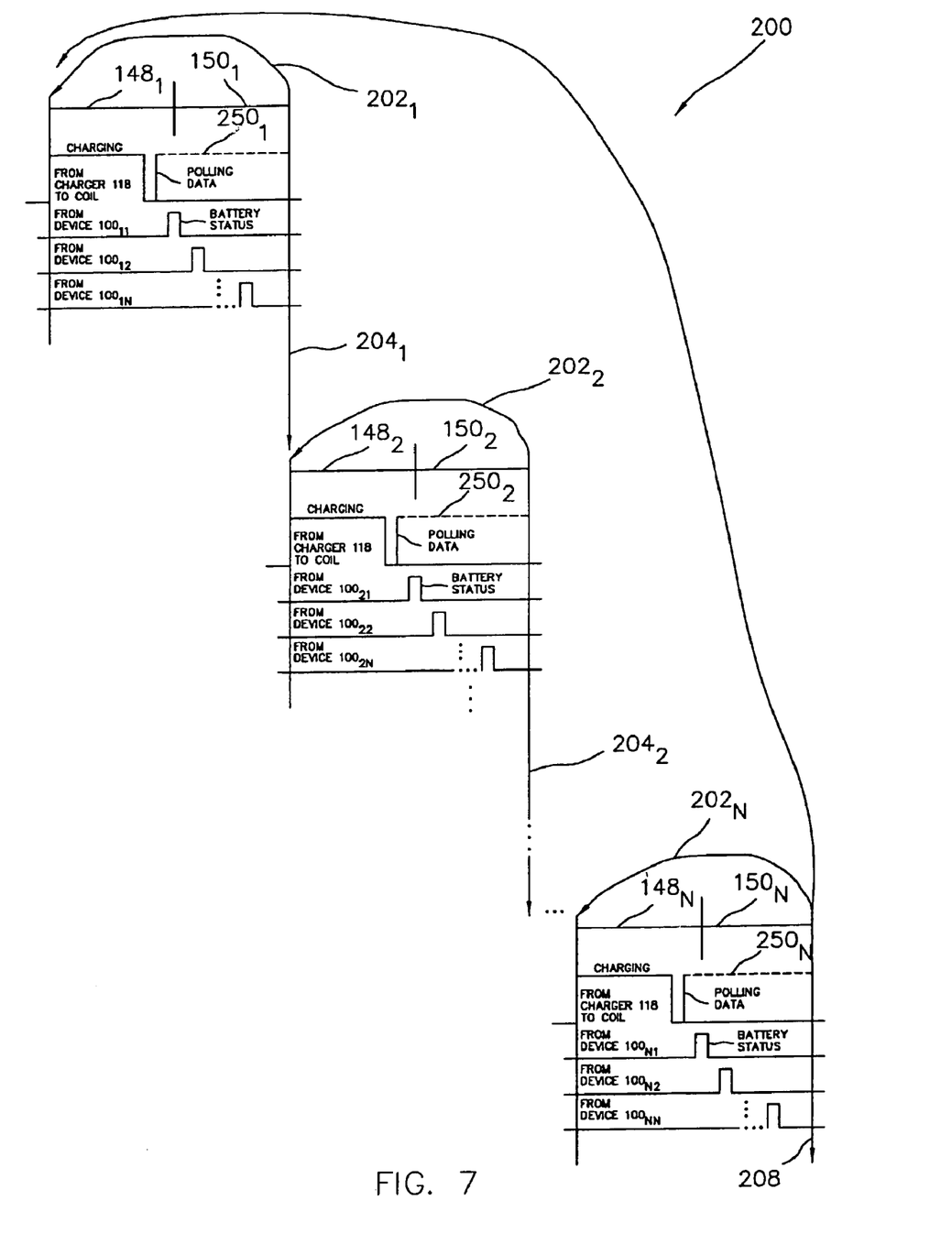
FIG. 7 shows a simplified timing diagram of a sequence for driving the coils of the embodiments of FIGS. 4–6.
Figure 8:
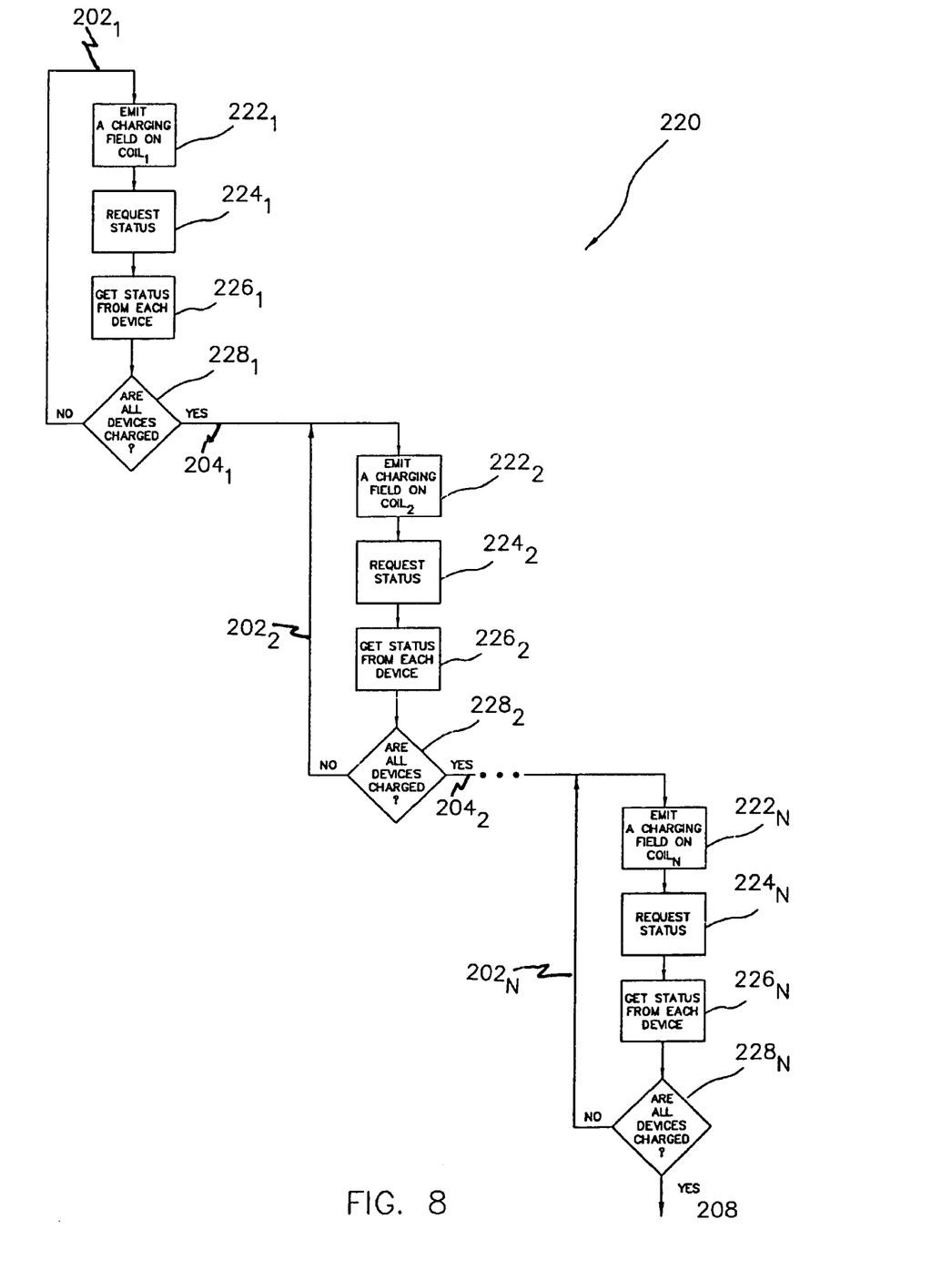
FIGS. 8–9 shows simplified block diagrams of two alternative processes for controlling the driving of the coils of the embodiments of FIGS. 4–6.

FIG. 7 shows a simplified timing diagram 200 of an exemplary sequence for driving the coils 158 of the embodiments of FIGS. 4–6. FIG. 8 shows a simplified block diagram 220 of the corresponding steps performed by the charger 118 in generating this sequence. In FIG. 7, the protocol described in reference to FIG. 3B is somewhat modified in accordance with the communication protocol described in commonly-owned U.S. patent application Ser. No. 09/882,603, filed Jun. 15, 2001, now U.S. Pat. No. 6,472,991, (hereinafter referred to as the '603 application), entitled "Multichannel Communication Protocol Configured To Extend The Battery Life Of An Implantable Device", the contents of which are incorporated herein by reference in their entirety. Characteristic of this protocol is that the implantable devices 100 respond to a status request from a system controller (in this case the charger 118) in time slots determined at least in part by their device ID. Since each device 100 has a unique ID, each device 100 will respond in a unique time slot following a polling data request from the charger 118. Accordingly, FIGS. 7 and 8 show the charger 118 powering a first coil, i.e., $coil_1$, during time period 148 (see block 222) and in discrete non-overlapping portions of time period 150 (determined by their respective device IDs in response to a status request in block 224), each device within the operational range of $coil_1$ responds with its respective battery status (see block 226). For the purpose of this figure, the device is designated with a subscript xy where x is the coil number and y is the 1-N of the device number of the devices within the operational range of the coil, e.g., device $100_{12}$ is the second device within the operational range of $coil_1$. Preferably, all of devices, even those within different operational ranges of the coils still have unique device IDs. In a first mode of operation, the charger 118 continues the operation with the selected coil until all of the devices 100 within its operational range respond that their respective batteries are charged (see block 228). This corresponds to repeating cycles 148, 150 continuously via repeat path 202. As previously discussed, individual devices 100 will preferably detune their coils 116 when their batteries 104 are fully charged so that their batteries 104 will not be damaged and so that excess heat will not be generated. Accordingly, the corresponding coil of charger 118 can still emit a charging field to charge the remaining devices 100.

Once all of the devices 100 within the operational range of one coil 158 indicate that they are charged, the charger 118 switches over to an essentially identical cycle for the next coil via next cycle path 204. The next cycle then repeats in a similar manner until all devices 100 are charged within the operational range of the next coil 158.

Once this process has been completed for each of the coils and each of the devices 100 within the operational range of each of their respective coils, the charging cycle is completed (see path 208).

Figure 9:
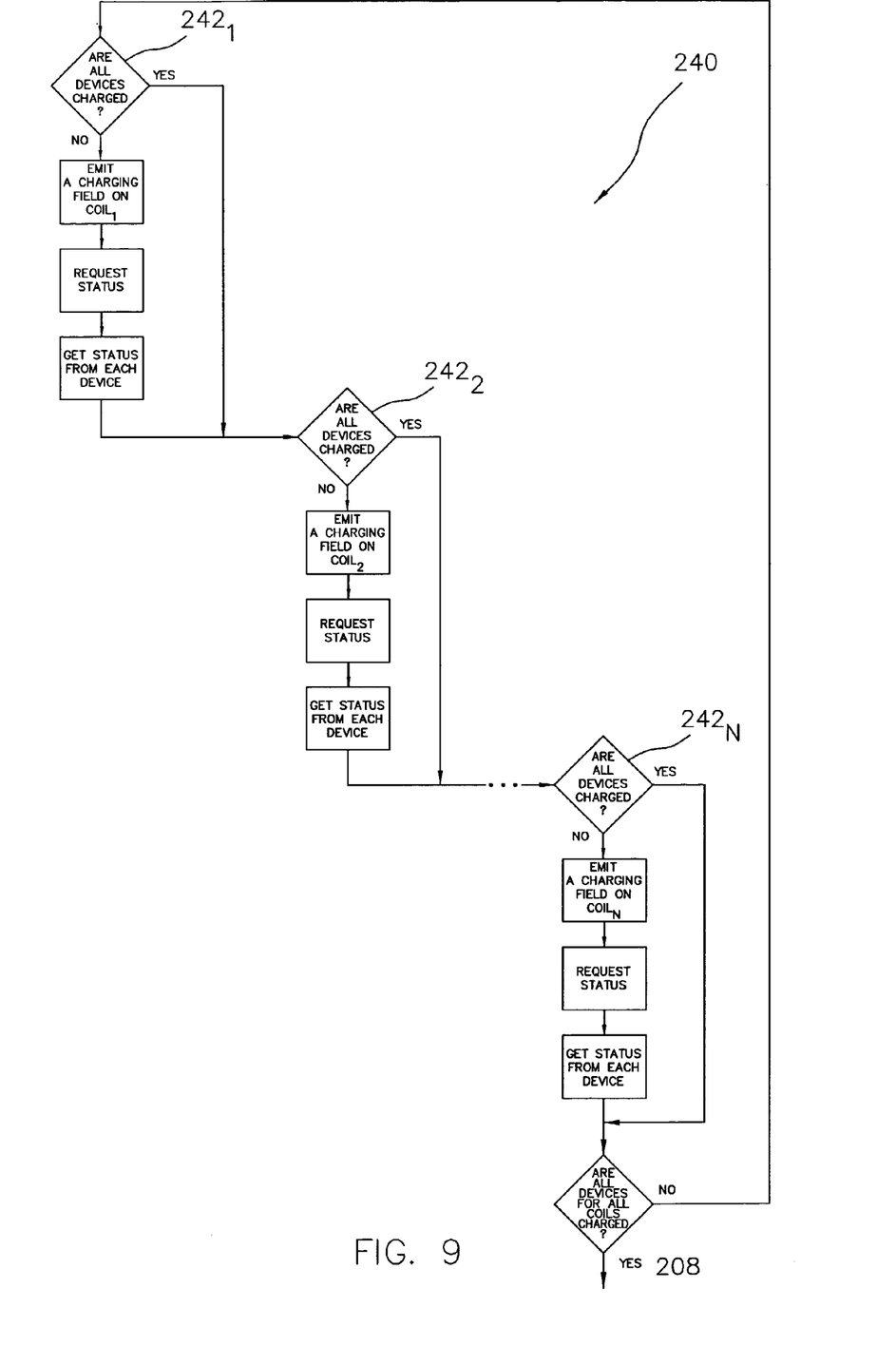

Alternatively (see FIG. 9), a second exemplary process 240 sequences through one coil 158 at a time determining whether all of the devices 100 in the operational range of each coil 158 are charged. Once the process 240 passes through each of the coils 158 and receives a fully charged status from each of the devices 100 within their respective operational ranges, the charging cycle is completed. Optionally (see block 242), the charger 118 may skip power cycles for an individual coil 158 if it determines that all of the devices 100 within its operational range were already charged during the prior cycle. Consequently, charging will be faster and less power will be used. Notably, in the process 240 of FIG. 9, all of the devices 100 will begin charging faster but it will be longer before any individual device 100 is charged.

When multiple communication modes/channels are used, full duplex communication may be achieved such that charging may occur essentially continuously, i.e., without breaks for receiving status communications from the implanted devices 100. Accordingly, while an alternating magnetic field with modulated command contained within may be used to supply power to recharge the batteries 104 in the implanted devices 100, a second communication channel, e.g., ultrasonic, propagated RF, etc., may be time shared by each of the implanted devices 100 to periodically provide status data without providing pauses in the charging field. Accordingly, in such a mode, the charging field may be presented essentially continuously (see the dashed lines $25O_1$–$25O_N$ of FIG. 7).

While the invention herein disclosed has been described by means of specific embodiments and applications thereof, numerous modifications and variations could be made thereto by those skilled in the art without departing from the scope of the invention set forth in the claims. For example, while full-body charging algorithms have been described that charge indefinitely until all of the devices within the operational range of the coils are fully charged, the algorithms can be easily modified to have a fail safe or predetermined time out, e.g., to charge for a maximum period of time and to abort independent of the battery status of the implantable devices or to charge for a fixed period time. It is therefore to be understood that within the scope of the claims, the invention may be practiced otherwise than as specifically described herein.

What is claimed is:

1. A full-body charger suitable for providing an alternating magnetic field to one or more electrically-powered devices adapted to be implanted beneath the skin of a patient's body wherein each electrically-powered device is powered by a rechargeable battery mounted within each electrically-powered device and each electrically-powered device includes circuitry for storing a unique identification address for each electrically-powered device, wherein each rechargeable battery is chargeable in response to said alternating magnetic field and each electrically-powered device includes circuitry for minimizing its response to said alternating magnetic field when the status of its rechargeable battery is fully charged and generating a fully-charged battery status signal in response thereto and wirelessly transmitting said status signal according to its unique identification address in response to a wirelessly received control signal, said charger comprising:

a support structure adapted to support a patient's body;

one or more coils configured for mounting within said support structure, proximate to one or more of the electrically-powered devices, for emitting a magnetic field substantially encompassing one or more of the electrically-powered implanted devices when one or more of the implanted devices are proximate to said support structure;

a controller for periodically providing an AC signal to energize at least one of said coils; and wherein said controller additionally includes communication circuitry for automatically periodically wirelessly providing a control signal to each electrically-powered device to selectively interrogate the status of the rechargeable battery mounted within and for wirelessly receiving a signal corresponding to the fully-charged battery status of the rechargeable battery in response thereto according to the unique identification address of each electrically-powered device.

2. The charger of claim 1 wherein said communication circuitry amplitude modulates said AC signal with said control signal and receives an AC signal amplitude modulated with the fully-charged battery status signal in response thereto.

3. The charger of claim 1 additionally comprising a transducer capable of emitting a modulated output signal and receiving a modulated input signal; and wherein said communication circuitry modulates the output of said transducer with said control signal and receives an input signal modulated with the fully-charged battery status signal in response thereto.

4. The charger of claim 1 wherein said support structure is chair-shaped.

5. The charger of claim 1 wherein said support structure is bed-shaped.

6. The charger of claim 1 wherein said coil is comprised of a plurality of conductive loops within said support structure.

7. The charger of claim 1 wherein said controller is configured for selectively energizing one of said coils at a time to generate a magnetic field that encompasses one or more of the electrically-powered devices within an operational range and to selectively query the fully-charged battery status of each electrically-powered device within said selected coil's operational range.

8. The charger of claim 7 wherein said controller is configured to sequentially energize one of said coils and query the fully-charged battery status of each of the electrically-powered devices within its operational range until all of the electrically-powered devices within its operational range indicate that their rechargeable batteries are fully charged and to then energize a different one of said coils.

9. The charger of claim 7 wherein said controller is configured to sequentially energize each of said coils until all of the electrically-powered devices indicate that their rechargeable batteries are fully charged.

10. The charger of claim 9 wherein said controller is configured to skip energizing a selected coil if during the selective query of the electrically-powered devices within said selected coil's operational range, all of the electrically-powered devices indicated that their batteries were fully charged.

11. A method suitable for charging rechargeable batteries mounted within one or more electrically-powered devices implanted beneath the skin of a patient's body via an alternating magnetic field and wherein each electrically-powered implanted device includes circuitry for minimizing its response to said alternating magnetic field when the status of its rechargeable battery is fully charged and generating a fully-charged battery status signal in response thereto, said method comprising the steps of:

positioning a patient, having one or more electrically-powered implanted devices, on a support structure proximate to at least one coil capable of being energized to emit an alternating magnetic field encompassing the one or more of the electrically-powered implanted devices;

energizing said at least one coil with an AC signal for a first time period to emit a magnetic field wherein the electrically-powered implanted devices are configured to charge their rechargeable batteries in response to said emitted magnetic field;

wirelessly emitting a control signal to the electrically-powered implanted devices during a second time period to selectively interrogate the status of the rechargeable battery mounted within one of the electrically-powered implanted devices according to a unique address for each of the electrically-powered implanted devices;

wirelessly receiving a fully-charged battery status signal from said selectively interrogated implanted device corresponding to its rechargeable battery during a third time period; and automatically repeating said energizing, emitting and receiving steps according to said fully-charged battery status signal received from each of said selectively interrogated implanted devices.

12. The method of claim 11 wherein said repeating step is terminated after a predefined time period.

13. The method of claim 11 wherein said wirelessly emitting step comprises modulating said AC signal with said control signal and using said modulated signal to energize said at least one coil.

14. A method suitable for charging rechargeable batteries mounted within one or more electrically-powered devices implanted beneath the skin of a patient's body in response to an alternating magnetic field when said patient's body is positioned on a support structure which includes a plurality of coils, each being capable of being energized to emit an alternating magnetic field encompassing the one or more of the electrically-powered implanted devices and wherein each electrically-powered device includes circuitry for minimizing its response to said alternating magnetic field when the status of its rechargeable battery is fully charged and generating a fully-charged battery status signal in response thereto, said method comprising the steps of:

(a) energizing a selected one of said coils with an AC signal for a first time period for providing charging power to the respective rechargeable battery of the electrically-powered implanted devices within an operational range;

(b) wirelessly emitting a control signal to the electrically-powered implanted devices during a second time period to selectively interrogate the fully-charged battery status of the rechargeable batteries mounted within the electrically-powered implanted devices located within said selected coil's operational range according to a unique address of each of the electrically-powered implanted devices;

(c) wirelessly receiving a fully-charged battery status signal from each of the electrically-powered implanted devices within said selected coil's operational range corresponding to the fully-charged battery status of its rechargeable battery during discrete portions of a third time period; and (d) automatically repeating said energizing, emitting and receiving steps according to said battery status signals received from each of the electrically-powered implanted devices until all of the electrically-powered implanted devices located within said selected coil's operational range indicate that their respective batteries are fully charged.

15. The method of claim 14 further comprising the step of:

(e) sequencing to a next selected one of said coils and repeating steps (a)–(d).

16. The method of claim 15 further comprising the step of:

(f) terminating the charging cycle when steps (a)–(d) have been executed for all of said coils.

17. A method suitable for charging rechargeable batteries mounted within one or more electrically-powered devices implanted beneath the skin of a patient's body in response to an alternating magnetic field when the patient's body is positioned on a support structure which includes a plurality of coils, each coil being capable of being energized to emit an alternating magnetic field encompassing one or more of the electrically-powered implanted devices and wherein each electrically-powered device includes circuitry for minimizing its response to said alternating magnetic field when the status of its rechargeable battery is fully-charged and generating a fully-charged battery status signal in response thereto, said method comprising the steps of:

(a) energizing a selected one of said coils with an AC signal for a first time period for providing charging power to the respective rechargeable battery of the electrically-powered implanted devices within an operational range;

(b) wirelessly emitting a control signal to the electrically-powered devices during a second time period to selectively interrogate the fully-charged battery status of the rechargeable batteries mounted within the electrically-powered implanted devices located within said selected coil's operational range according to a unique address of each of the electrically-powered implanted devices;

(c) wirelessly receiving a fully-charged battery status signal from each of the electrically-powered implanted devices within said selected coil's operational range corresponding to the fully-charged battery status of its rechargeable battery during discrete portions of a third time period; and (d) automatically repeating steps (a)–(c) for a different selected one of said coils.

18. The method of claim 17 further comprising the step of:

(e) repeating steps (a)–(d) until the last one of said plurality of coils has been selected and then sequencing to the first one of said plurality of coils if any one of the electrically-powered implanted devices has indicated that its battery is not fully charged.

19. The method of claim 18 further comprising the step of:

(f) skipping steps (a)–(c) for a selected coil if the last fully-charged battery status signals received for each of the electrically-powered implanted devices within said selected coil's operational range indicated that all of the rechargeable batteries within the selected coil's operational range were fully charged.

20. The method of claim 17 wherein steps (a)–(d) are repeated for a prescribed maximum length of time.

* * * * *